United States Patent [19]

Portmann et al.

[11] Patent Number: 5,540,891
[45] Date of Patent: Jul. 30, 1996

[54] MULTI-WELL TITERPLATE FOR INSTRUMENTAL ANALYSIS

[75] Inventors: Rudolf Portmann, Bern; Andreas Hirschi, Interlaken; Andreas Wellenreiter, Wilderswil, all of Switzerland

[73] Assignee: Scheizerische Eidgenossenschaft vertreten durch das AC-Laboratorium Spiez der Gruppe fur Rustungsdienste, Spiez, Switzerland

[21] Appl. No.: 321,395

[22] Filed: Oct. 11, 1994

[30] Foreign Application Priority Data

Oct. 18, 1993 [CH] Switzerland ............... 03141/93

[51] Int. Cl.$^6$ ................... B01L 3/00; B01L 9/00
[52] U.S. Cl. ............... 422/102; 422/99; 422/101; 422/104; 435/1; 435/305.2; 264/138; 206/443; 206/446; 211/74; 220/528; 220/533; 220/507; 220/527; 220/610; 220/611
[58] Field of Search ................... 422/101, 102, 422/99; 220/528, 529, 533, 527, 507, 611, 610, 507; 206/443, 446; 211/74; 435/301; 356/244, 246; 264/138, 219, 333

[56] References Cited

U.S. PATENT DOCUMENTS

| | | | |
|---|---|---|---|
| Re. 34,133 | 11/1992 | Thorne | 422/99 |
| 3,649,464 | 3/1972 | Freeman | 220/507 |
| 4,154,795 | 5/1979 | Thorne | 422/99 |
| 4,385,115 | 5/1983 | de Zabala et al. | 435/33 |
| 4,526,690 | 7/1985 | Kiovsky et al. | 210/335 |
| 4,902,481 | 2/1990 | Clark et al. | 422/101 |
| 4,968,625 | 11/1990 | Smith et al. | 435/301 |
| 5,187,096 | 2/1993 | Giaever et al. | 435/291 |
| 5,265,754 | 11/1993 | Dalbo | 220/524 |
| 5,326,533 | 7/1994 | Lee et al. | 422/101 |

FOREIGN PATENT DOCUMENTS 2819820  11/1978  Germany.

Primary Examiner—Jill Warden
Assistant Examiner—Harold Y. Pyon
Attorney, Agent, or Firm—Schweitzer Cornman & Gross

[57] ABSTRACT

A titerplate for instrumental analysis of liquid samples consists of a plurality of wells in which the walls and bottoms are made of two different materials with different physical properties. This allows the interfacial tension at the surface of the liquid to be controlled in such a way that it is essentially planar, allowing more accurate analysis to be performed on the samples. The bottoms of the wells are preferably made of a transparent material, so that the analysis and observation can be done in the transmission mode.

10 Claims, 4 Drawing Sheets

5,540,891

MULTI-WELL TITERPLATE FOR INSTRUMENTAL ANALYSIS

The present invention relates to a titerplate of a multi-well configuration. The disclosure of Swiss patent application No. 03 141/93-6, filed Oct. 18, 1993, of which priority is claimed, is incorporated herein by reference.

BACKGROUND OF THE INVENTION

Titerplates, and especially microtiterplates, are used more and more in the instrumental analysis of samples. Yet, it has been shown that the use of well known methods of photometric evaluation, such as the ELISA test (Enzyme Linked Immunosorbant Assay), the determination of enzyme activity, etc., is often hampered, or the results falsified, by a meniscus which is formed on the surface of mostly aqueous samples subject to evaluation. The formation of a meniscus is the result of surface- and interfacial-tensions and, as a consequence of the wettability of the surfaces contacted by the liquid, the meniscus can be convex or concave.

It is therefore the purpose of the present invention to create a multi-well structure for titerplates and the like which reduces to an acceptable level or prevents the formation of an interfering meniscus on the liquid surface, while not appreciably absorbing the instrumental analysis light ray, nor influencing the light path.

BRIEF DESCRIPTION OF THE INVENTION

In accordance with the present invention, materials having different physical properties are combined into an arrangement wherein the walls and the bottoms of the wells are joined in a manner in which the sample to be analyzed forms a boundary angle of about 90 degrees between the liquid and the wall. The bottoms of the wells are further configured to allow the rays used to pass therethrough without reflections which can falsify the evaluation.

In accordance with the invention, a variety of a multitude of suitable material combinations can be assembled.

The use of an apolar thermoplast for the well walls and a transparent thermoplast for the well bottoms provides a preferred construction for the observation of aqueous, and therefore polar, samples. Well bottoms can be formed as a matrix of elevations in a plate-like element. The well walls can be mounted thereon with a friction fit to minimize or avoid welding or gluing. Such a formation also allows an indexing system of coordinates to be used to locate and identify the samples.

In a preferred embodiment, sub-assemblies having a plurality of well walls may be mounted upon a base plate and elevation unit to form a large-scale multi-element plate system. The assemblies may be provided with holes or apertures through which indexing spigot shafts extend to align and mount the sub-assemblies to a base plate element.

BRIEF DESCRIPTION OF THE DRAWINGS

In the following description the objects and features of the invention will be explained in more detail, and may be reviewed in conjunction with the annexed drawings, in which.

DETAILED DESCRIPTION OF THE INVENTION

Figure 1:
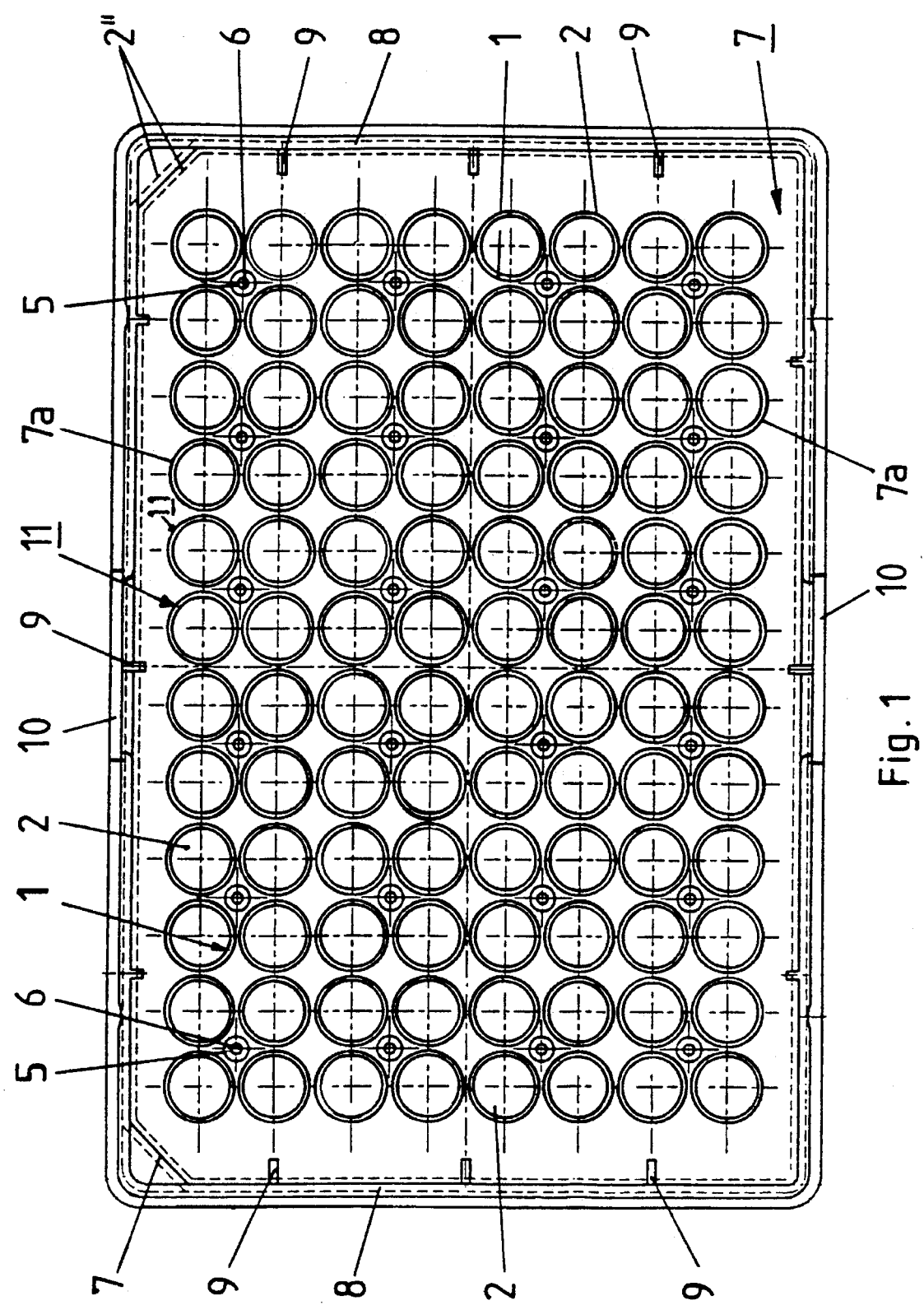
FIG. 1 depicts in a plan view a microtiter plate in accordance with the invention with a transparent protective cover.

Referring initially to FIG. 1, a multi-well titerplate assembly is shown having an array of 96 individual wells 11. Each well includes a well bottom 2 preferably formed as part of a plate or sheet-like bottom plate structure 2' and an upstanding cylindrical wall 1, which may be similarly formed as part of a multi-well forming element. The array of well bottoms lie in a common plane. A series of vertical distance-gauging elements or shafts 6 extend upwardly from the bottom plate 2' and are aligned with spigot holes 5 formed in the wall forming elements. An overlying frame cover 7 includes holes 7a for the upper ends of the well walls 1. The well bottoms are typically transparent, and, along with the walls, may be provided at least partially with a surface adapted to adsorb the sample to be placed therein, as known in the art.

The frame cover 7 further includes supports and guide webs in the form of edge straps or pieces 9. The frame cover exterior is typically provided with opposed grip areas 10 positioned above a peripheral supporting lower rim or web 8.

Figure 2:
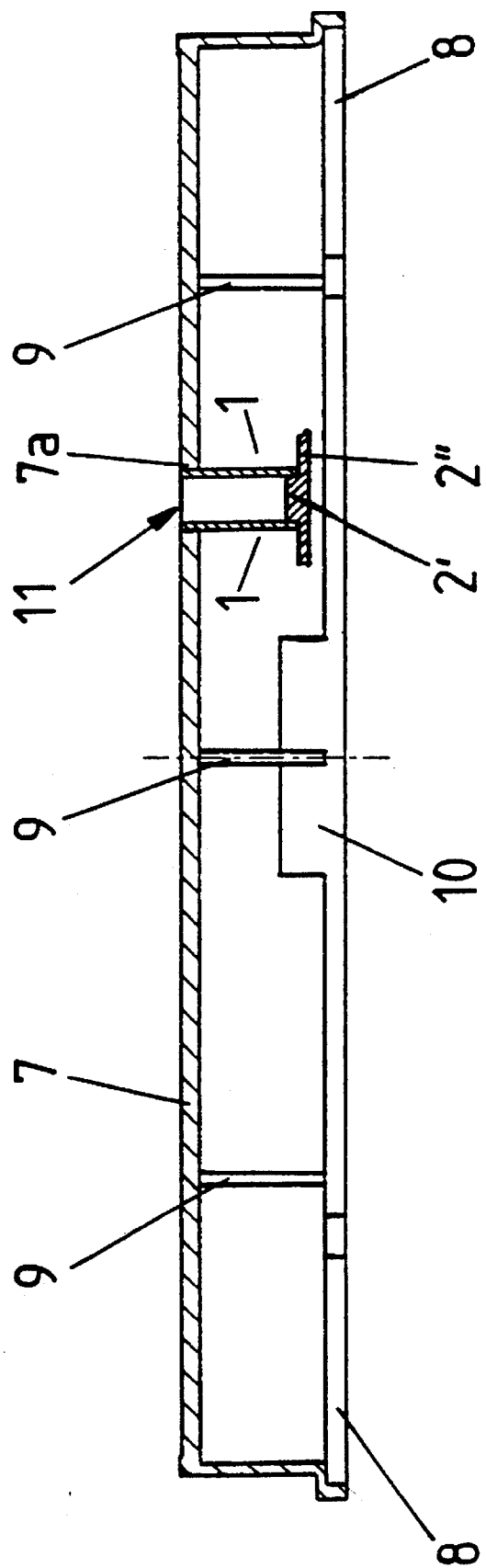
FIG. 2 presents a simplified vertical sectional view through the microtiter plate of FIG. 1 in the longitudinal axis with a representative well depicted.

As best seen in the sectional view of FIG. 2, the frame cover 7 is shown supported by its peripheral wall and surrounding supporting rim or web 8 in a manner whereby an upstanding well wall 1 is embraced in a friction fit by the hole 7a. Each of the wells 11 is aligned with a hole 7a, each well wall further surrounding and enclosing one of the plug-like elevations 2 which are arranged on the base plate 2". The walls 1 project through the frame cover 7, through the holes 7a.

Figure 3:
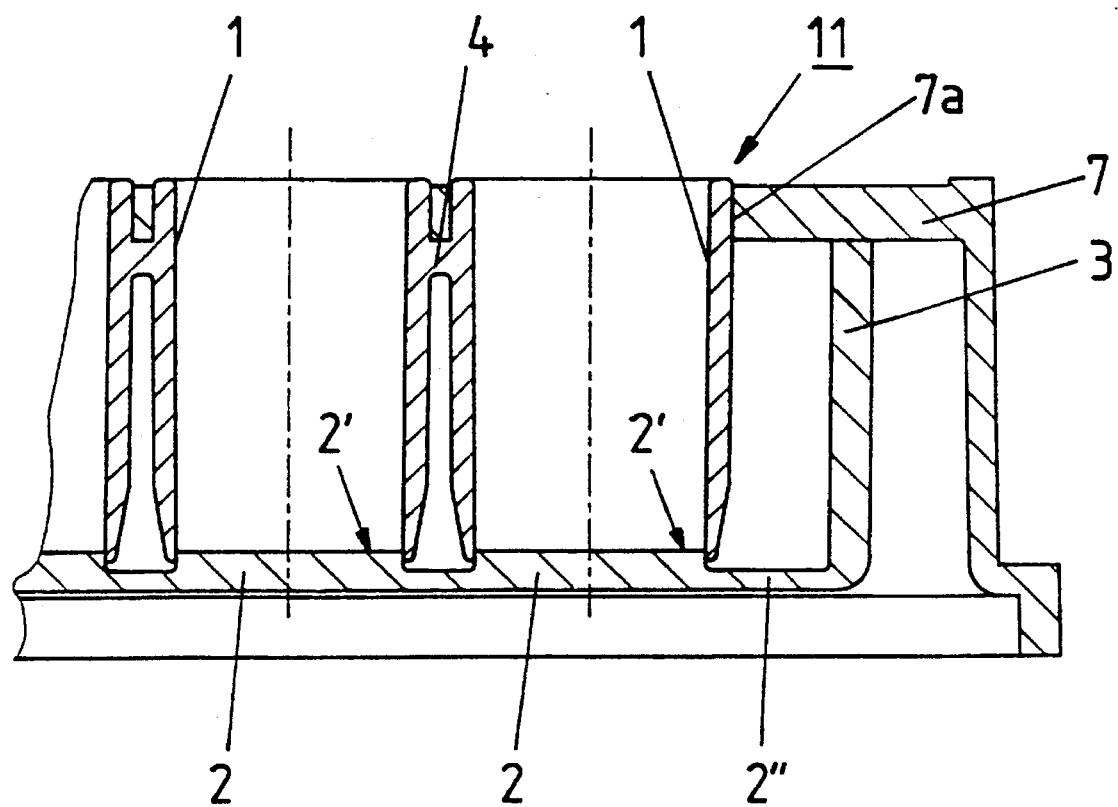
FIG. 3 is a magnified presentation of a partial sectional view through the microtiter plate of FIG. 1.
Figure 4:
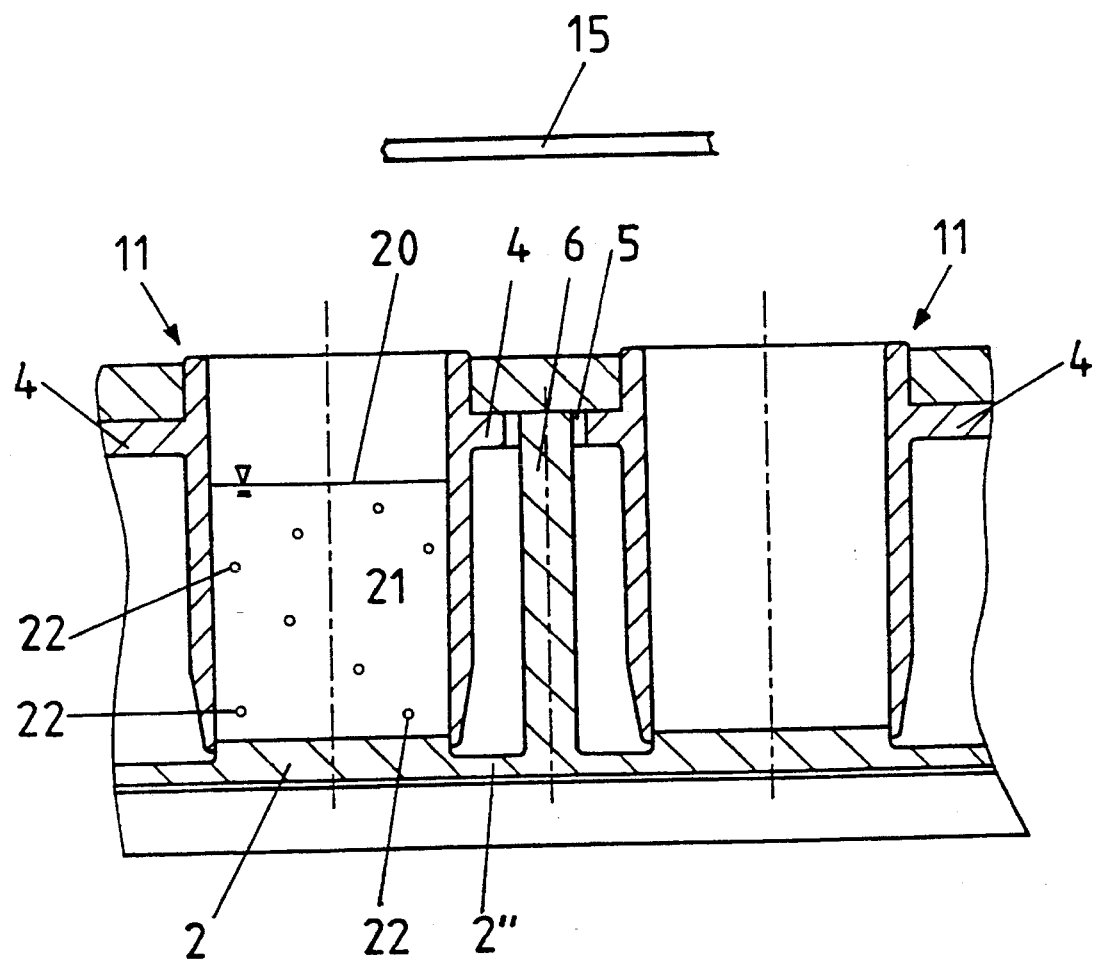
FIG. 4 is a partial sectional view through the microtiter plate of FIG. 1 further detailing the structure of the present invention.

FIGS. 3 and 4 further present the elements of the construction in greater detail. As seen therein, a connecting web 4 may be provided between the well walls 1 and allows a plurality of well walls to be formed as a unitary element. The height of the well walls 1 is chosen such that the walls are not directly touching the base (bottom) plate 2" and protrude only slightly above the frame cover 7 through its holes 7a. The plugs or elevations 2' are formed as integral raised portions upon the bottom plate 2", and define the bottoms 2 for the wells. The elevations are peripherally sealed by the well walls 1 to form the liquid-tight wells. It can be seen that the lower portion of the walls 1 receive an outside cone-shaped taper to obtain an additional desired elasticity or suppleness at such a lower end zone, permitting a snug fit about the elevations 2' to be obtained.

The bottom plate 2" is surrounded by an upturned lip or border 3 and forms a generally box-shaped peripheral supporting dish or shell, the border 3 simultaneously serving as a distance-defining element or spacer for the frame cover 7, as depicted in the right region of FIG. 3, assisting in the positioning and alignment of the cover with respect to the well walls 1. It is to be recognized that the cover allows the bottom plate 2" to be supported above the surface upon which the frame cover sits.

As seen in FIG. 4, a wall assembly 11 preferentially having 16 wall elements 1 joined by the connector or web 4, is guided during its mounting onto the associated elevations 2 by a series of spigot holes 5 located in the centers of the connecting pieces or webs 4 mating with the spigot shaft/ distance elements 6 extending upwardly from the bottom plate 2". Upon assembly, the spigot shaft elements 6 are free in the spigot holes 5, as can be deduced from FIG. 4. By aligning the top ends of the shafts with the top surface of the web 4 the shaft serves to properly space the frame cover 7 from the bottom plate 2" since the frame cover is supported in a frictional fit with the tops of the well walls 1. Also depicted in FIG. 4, above the layout, is a protective cover 15 which, by the design of its border, can be configured to be mounted only in one orientation on the lay-out, as clearly depicted in FIG. 1. With a single orientation, the cover can be provided with indicia to identify the cells. Alternatively, the cell walls or the webs between the walls can be marked as desired.

Preferred construction materials are polystyrene type BASF SB 475K for the bottom plate and polypropylene type BASF PP 1324 M or polypropylene type BASF PP 1325 L for the walls of the wells; for the frame cover 7, polystyrene type BASF PS 144C gave satisfactory results. All parts are manufactured by commonly known pressure casting techniques. Such apolar materials allow aqueous (polar) samples, such as the liquid sample 21 containing organisms 22 as depicted in FIG. 4, to have a planar top surface 22 allowing for improved observation and analysis.

In mounting the well walls 1 it is preferred to use expanding mandrels, as known in the art, to allow the well walls to be slid over the elevations 2' without interference. This allows a tight connection to be formed without the use of glues or laborious welding techniques. The technique can be used to join a variety of so-called "unconnectable" plastics and other materials. Alternatively, heat expansion can be used during mounting.

Using materials of the type set forth above, a well layout for aqueous salt test solutions comprising 405.0 mM NaCl, 18.9 mM $MgSO_4*7H_2O$, 16.4 mM $MgCl_2*6H_2O$, 7.3 mM $CaCl_2*2H_2O$, 1.59 mM $NaHCO_3$ and 6.65 mM KCl were constructed with an overall size of 125×80 mm and a height of 15 mm. The wells were of 8.5 mm outer diameter and 7 mm inside diameter with a depth (height) of 9.5 mm.

The construction materials were evaluated for meniscus formation using a known method of video observation in the transmission mode. No meniscus was observed as being formed through 48 hours, using the above-mentioned aqueous salt solution.

It may be necessary in certain circumstances to sterilize the lay-out, and in particular the wells, using appropriate irradiation techniques. When gamma(γ)irradiation is used, it is recommended that the walls be made of a material resistant to such radiation, such as BOREALIS VT 1064 KN polypropylene.

With transparent well bottoms, the invention has particular utility and value in conjunction with video observation and analysis in the transmission mode, wherein a video camera is preferably mounted below the bottoms of the wells. Shadow and contrast problems as encountered with common titerplates can be completely eliminated by the present invention.

We claim:

1. A multi-well titerplate assembly for use in conjunction with instrumental analysis is of liquid samples, comprising a plurality of individual wells each having a side wall and a bottom, said bottoms being arrayed in a common plane and being formed as a series of elevations upon a bottom plate, said side wall being of an apolar thermoplastic material chosen to interact with a liquid sample to be placed within the well whereby the resulting interfacial tension between the sample and the well side wall results in a generally planar sample surface, the material for the well bottom being a transparent thermoplastic material chosen to allow observation and analysis of the sample therethrough, the side wall being mounted with a friction-fit about the periphery of the wall bottom.

2. The assembly of claim 1, wherein the well wall material is chosen from the group consisting of polyolefin or polytetrafluoroethylene and the well bottoms are constructed of a material chosen from the group consisting of polystyrene, polystyrene co-polymer, polymethylmethacrylate, polycarbonate, polyethersulfone, polysulfone, polysulfone, polymethylpentene, styreneacrylnitrile, amorphous polyamid and polymethylentherephtalate.

3. The apparatus according to claim 1, wherein at least one of the wall and bottom of a well comprise a sample-adsorbing surface.

4. The apparatus according to claim 1, wherein at least two of said well walls are mechanically connected to form an individual sub-assembly unit.

5. The apparatus of claim 1 further comprising means associated with each of the wells to identify each well and samples placed therein.

6. The apparatus according to claim 5, wherein said means comprise a common protective cover.

7. The apparatus of claim 1, further comprising at least one alignment shaft extending vertically upward from said bottom plate, wherein said individual sub-assembly element includes at least one spigot hole for mounting upon one of said alignment shafts.

8. The apparatus of claim 7, wherein said sub-assembly unit comprises a web portion joining the well walls, said at least one spigot hole being located in said web, said web being located vertically along said well walls to vertically align said sub-assembly unit with respect to said elevations when an end of said alignment shaft is co-planar with a top surface of said web.

9. The apparatus of claim 8 further comprising a top plate and a peripheral depending lip, said top plate having a series of holes therein each located and dimensioned to accept a top portion of a well wall.

10. The apparatus of claim 9, wherein said top surface of said web is adapted to support said top plate.

* * * * *